(12) United States Patent
Cronin et al.

(10) Patent No.: US 7,691,150 B2
(45) Date of Patent: Apr. 6, 2010

(54) MODULAR PLATE AND KEEL PROVISIONALS

(75) Inventors: Shaun R. Cronin, Fort Wayne, IN (US); Scott E. Dykema, Warsaw, IN (US); Jeff Blaylock, Fort Wayne, IN (US); Buddy E. Kaczewzki, Leesburg, IN (US); John E. Meyers, Columbia City, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 29 days.

(21) Appl. No.: 11/611,196

(22) Filed: Dec. 15, 2006

(65) Prior Publication Data

US 2008/0147203 A1 Jun. 19, 2008

(51) Int. Cl.
*A61F 2/38* (2006.01)
(52) U.S. Cl. .................................. 623/20.32; 623/20.34
(58) Field of Classification Search .............. 623/20.15, 623/20.32–20.36, 20.14
See application file for complete search history.

(56) References Cited

U.S. PATENT DOCUMENTS

| | | | | |
|---|---|---|---|---|
| 5,067,956 | A | * | 11/1991 | Buford et al. ............... 606/289 |
| 6,258,127 | B1 | * | 7/2001 | Schmotzer ............... 623/20.32 |
| 2003/0055508 | A1 | * | 3/2003 | Metzger et al. ........... 623/20.15 |
| 2004/0073315 | A1 | | 4/2004 | Justin et al. |
| 2004/0249467 | A1 | | 12/2004 | Meyers et al. |
| 2005/0203631 | A1 | | 9/2005 | Daniels et al. |
| 2005/0203632 | A1 | | 9/2005 | Daniels |
| 2005/0283252 | A1 | | 12/2005 | Coon et al. |
| 2007/0162145 | A1 | | 7/2007 | Justin et al. |
| 2007/0203582 | A1 | * | 8/2007 | Campbell ................ 623/20.34 |

* cited by examiner

*Primary Examiner*—Corrine M McDermott
*Assistant Examiner*—Megan Wolf
(74) *Attorney, Agent, or Firm*—Baker & Daniels LLP (57) ABSTRACT

A provisional prosthetic system and the surgical methods for utilizing the same. In one embodiment, the provisional prosthetic system includes a keel and a plate configured to be secured to the keel. The keel may further include a body and at least one fin extending outwardly therefrom. The fin functions to prevent rotation of the keel once it is implanted within a bone. In one embodiment, the plate includes a captured screw having a flanged head and external threads. The captured screw is retained by the plate and configured to secure the plate to the keel. In this embodiment, the captured screw extends through an aperture in the plate. Further, the captured screw may be retained by the plate due to the interaction of the flange head and external threads of the captured screw with the top and bottom surfaces of the plate, respectively.

11 Claims, 6 Drawing Sheets

FIG_1

FIG_2

FIG_3

FIG_5

FIG_4

FIG_6

FIG_7

FIG_8

FIG_9

FIG_10

FIG_11

FIG_12

FIG_13

FIG_14

FIG_17

MODULAR PLATE AND KEEL PROVISIONALS

BACKGROUND

1. Field of the Invention

The present invention relates to a provisional prosthetic system and the surgical methods for utilizing the same.

2. Description of the Related Art

Prostheses are commonly utilized to repair and/or replace damaged bone and tissue in the human body. For example, a knee prosthesis may be implanted to replace damaged or destroyed bone in the tibia and/or femur and to recreate the natural, anatomical articulation of the knee joint. To implant a prosthesis, orthopedic surgery is performed which requires the creation of an incision in the skin of the patient and may necessitate the retraction of surrounding tissue to provide the surgeon with access to the surgical site.

To facilitate the implantation of a prosthesis, modular prostheses may be utilized. Modular prostheses have several individual, distinct components which are connected together to form the final, implanted prosthesis. Additionally, one component, i.e., a tibial plate in a modular tibial prosthesis system, may be selected from several different tibial plate components having various configurations, all of which are included in the modular prosthesis system. By selecting the tibial plate that best accommodates the individual patient's anatomy, the surgeon may assemble a prosthesis that more closely approximates the patient's anatomy.

In addition to the final, implanted components of a modular prosthesis system, a modular prosthesis system may also include trial or provisional components which replicate the size and shape of the final, implanted components of the modular prosthesis system. The use of provisional components provides the surgeon with the ability to test the ultimate configuration of the prosthesis prior to the implantation of the final components. By trialing, i.e., testing, the surgeon is able to determine whether that the fit, alignment, and range of motion provided by the final prosthesis will approximate the patient's natural anatomy.

SUMMARY

The present invention relates to a provisional prosthetic system and the surgical methods for utilizing the same. In one embodiment, the provisional prosthetic system includes a keel and a plate configured to be secured to the keel. The keel may further include a body and at least one fin extending outwardly therefrom. The fin functions to prevent rotation of the keel once it is implanted within a bone. In one embodiment, the plate includes a captured screw having a flanged head and external threads. The captured screw is retained by the plate and configured to secure the plate to the keel. In this embodiment, the captured screw extends through an aperture in the plate. Further, the captured screw may be retained by the plate due to the interaction of the flange head and external threads of the captured screw with the top and bottom surfaces of the plate, respectively.

In another exemplary embodiment, the plate includes a recess configured to receive a portion of the keel therein. When the keel is received within the recess of the plate, the wall defining the recess of the plate may abut the body and/or at least one fin of the keel to ensure that the plate and the keel are properly aligned. In a further embodiment, the plate may include an alignment aperture extending therethrough. When the plate is properly aligned relative to the keel, a portion of the keel is visible through the alignment aperture of the plate.

Advantageously, the design of the present provisional prosthetic system allows a surgeon to ensure that proper alignment between the plate and the keel has been obtained. As a result, the trialing of the provisional components by the surgeon accurately replicates the function of the final implants. Additionally, the use of a captured screw prevents the screw from becoming disengaged during surgery and, as a result, reduces surgical time.

In one form thereof, the present invention provides a provisional prosthetic system, including a keel sized to replicate the orientation of at least one component of a modular prosthesis, a plate sized to replicate the orientation of at least another component of a modular prosthesis, said plate having an aperture extending therethrough, and a captured screw retained through said aperture in said plate, whereby said plate limits axial movement of said captured screw, said captured screw configured to secure said plate to said keel.

In another form thereof, the present invention provides a provisional prosthetic system, including a keel sized to replicate the orientation of at least one component of a modular prosthesis, said keel having a fin extending therefrom, a plate sized to replicate the orientation of at least another component of a modular prosthesis, said plate configured to be secured to said keel, said plate having an aperture extending therethrough, wherein said fin of said keel is visible through said aperture when said plate is properly aligned with said keel.

In yet another form thereof, the present invention provides a method of assembling a provisional prosthetic component, including the steps of orienting a plate relative to a fin extending from a keel, the plate sized to replicate the orientation of at least one component of a modular prosthesis and the keel sized to replicate the orientation of at least another component of a modular prosthesis, visually confirming that the plate is properly oriented with respect to the fin of the keel through an aperture in the plate, and securing the plate to the keel with a captured screw.

BRIEF DESCRIPTION

The above-mentioned and other features and advantages of this invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION

Figure 1:
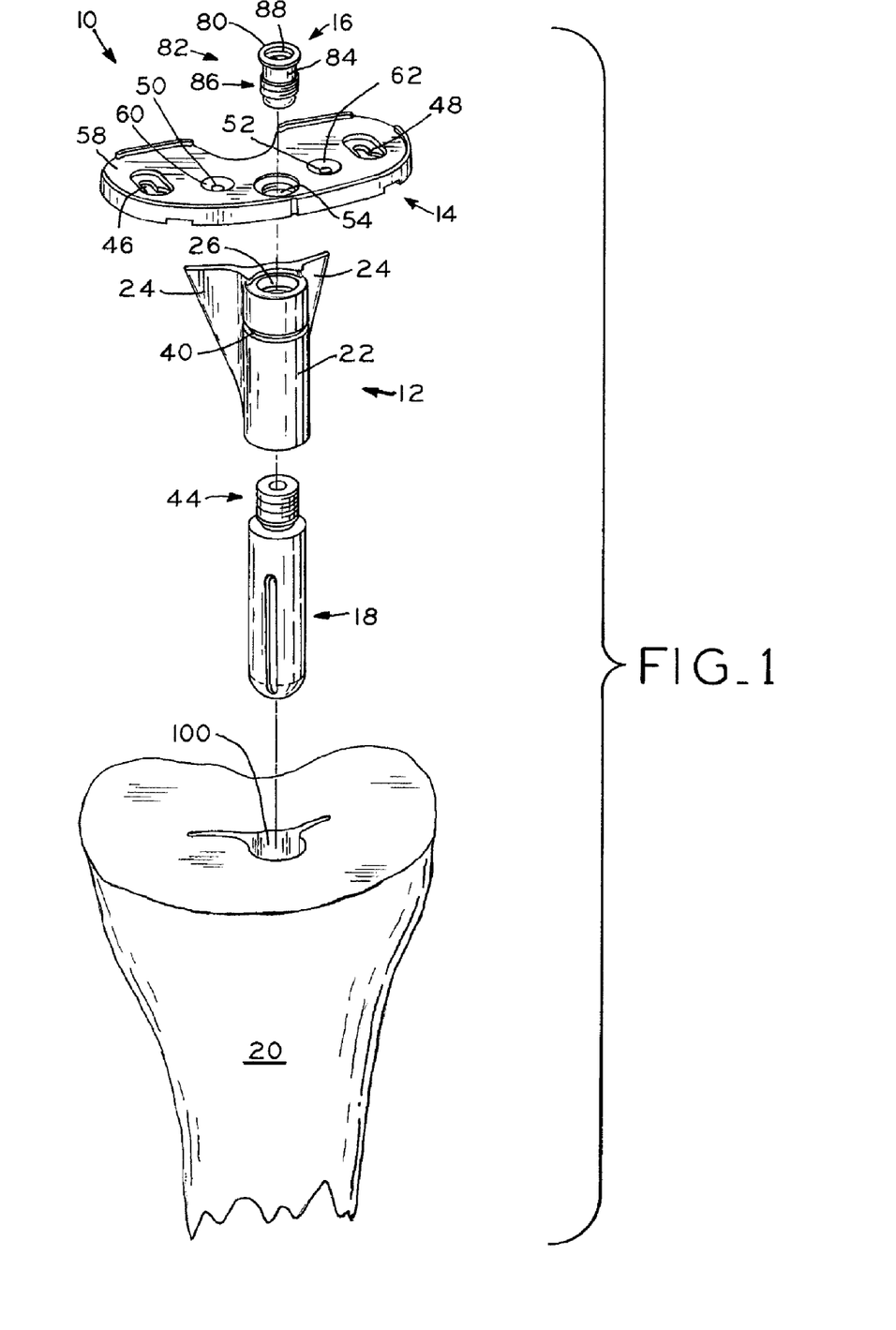
FIG. 1 is an exploded view of a provisional prosthetic system according to the present invention positioned adjacent a tibia.

FIG. 1 depicts an exploded view of provisional prosthetic system 10 including keel 12, plate 14, and captured screw 16. While provisional prosthetic system 10 is described as depicted herein with specific reference to captured screw 16, any known securement device may also be utilized, such as bolts or other screws. As depicted in FIG. 1, provisional prosthetic system 10 also includes stem 18. Stem 18 may optionally be attached to keel 12 to provide additional stabilization to provisional prosthetic 10 and to replicate the orientation of the final, implanted components. Provisional prosthetic system 10 is designed and configured for implantation within tibia 20, shown in FIG. 1. While provisional prosthetic system 10 is described and depicted herein with specific reference to tibia 20, provisional prosthetic system 10 can be utilized in conjunction with other tissue, such as the glenoid. Additionally, the teachings of the present system may be utilized with other prosthetic components.

Figure 2:
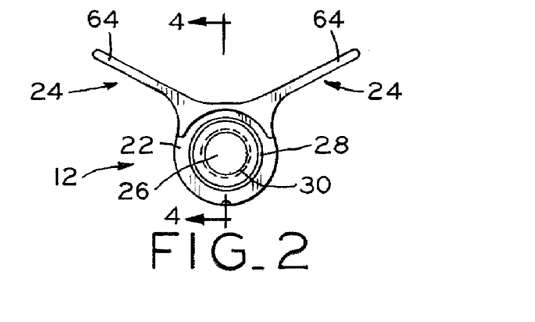
FIG. 2 is a plan view of the keel of the provisional prosthetic system of FIG. 1.
Figure 3:
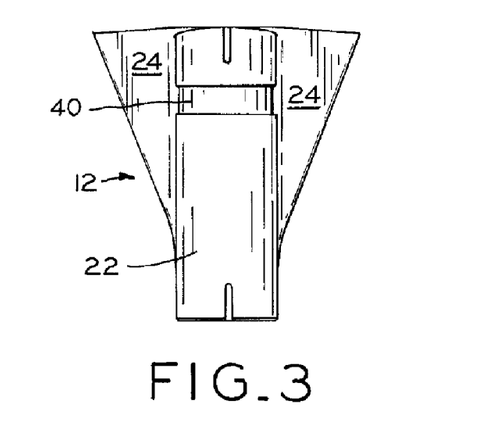
FIG. 3 is a front view of the keel of FIG. 2.
Figure 4:
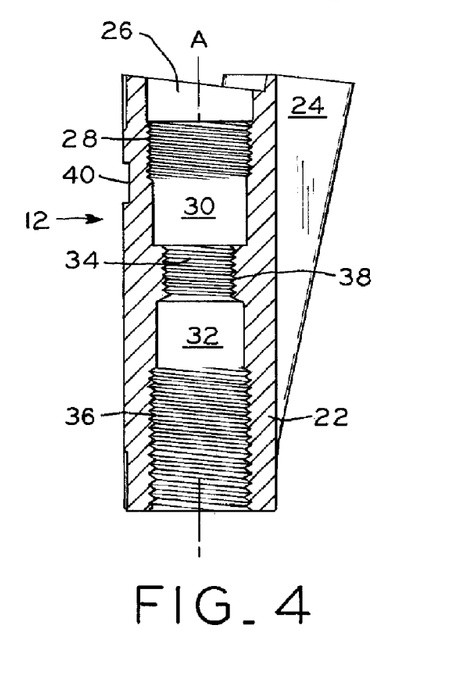
FIG. 4 is a cross-sectional view of the keel of FIG. 2, taken along line 4-4 of FIG. 2.
Figure 17:
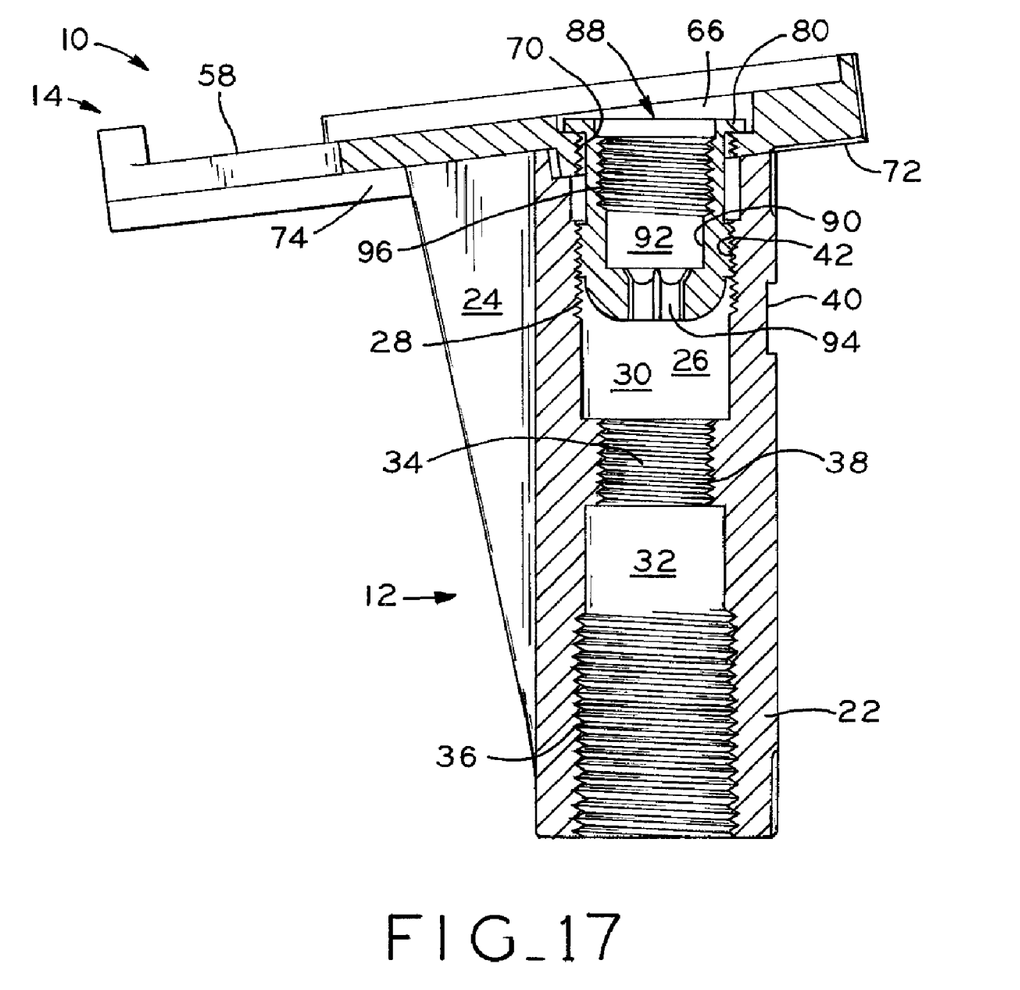
FIG. 17 is a cross-sectional view of the assembled provisional prosthetic system of FIG. 1.

Keel 12 of provisional prosthetic system 10, as depicted in FIGS. 2-4, includes body 22 and fins 24. In one embodiment, keel 12 is one of a plurality of keels 12 sized to replicate the orientation of at least one component of a modular prostheses. Fins 24 extend outwardly from body 22 and are configured to prevent rotation of keel 12 after insertion into tibia 20. Keel 12 also includes internal bore 26 formed therein and, as shown in FIGS. 4 and 17, bore 26 extends entirely through keel 12. Referring to FIGS. 4 and 17, internal bore 26 extends along longitudinal axis A (FIG. 4) and includes captured screw engaging threaded portion 28 formed within first counterbore 30. The threads of internal bore 26 further includes second counterbore 32 and connecting portion 34. Second counterbore 32 and connecting portion 34 include stem engaging threads 36 and extraction tool engaging threads 38, respectively. Stem engaging threads 36 of second counterbore portion 32 are configured to engage threaded shaft 44 of stem 18 (FIG. 1). Engagement of threads 36 with threaded shaft 44 provides securement of stem 18 to keel 12. Keel 12 also includes groove 40 formed on the exterior of body 22 configured for engagement with a keel holder (not shown). Captured screw engaging threaded portion 28 is configured for mating engagement with external threads 42 of captured screw 16, shown in FIGS. 1 and 11-14 and discussed in detail below. Similarly, extraction tool engaging threads 38 of connecting portion 34 are configured to engage the threads on an extraction tool (not shown). Providing extraction tool engaging threads 38 within keel 12 allows for the independent removal of keel 12 from tibia 20. Thus, a surgeon can remove plate 14 to independently check the alignment or position of keel 12 and then remove keel 12 without the need to reattach plate 14 for removal.

Figure 5:
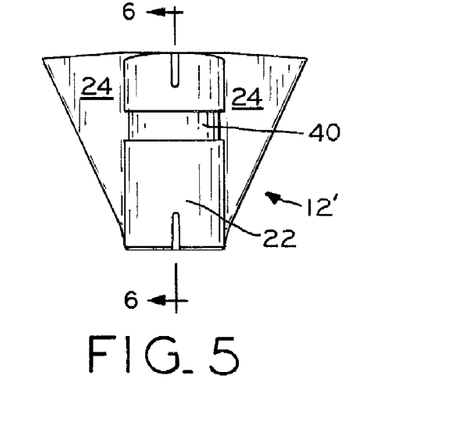
FIG. 5 is a front view of a keel of the provisional prosthetic system of FIG. 1 according to another embodiment.
Figure 6:
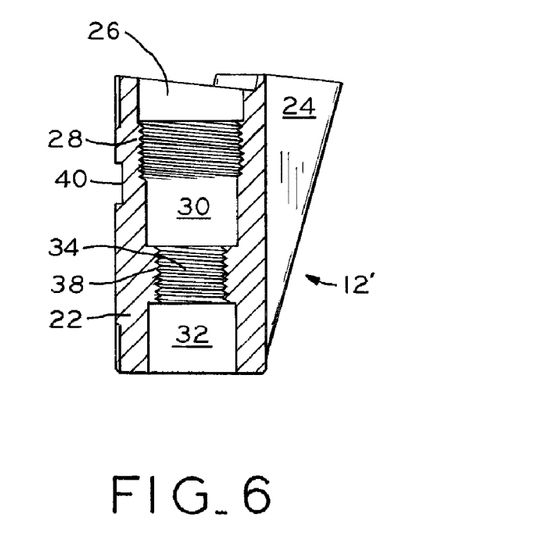
FIG. 6 is cross-sectional view of the keel of FIG. 5 taken along line 6-6 of FIG. 5.

FIGS. 5 and 6 depict an alternate embodiment of keel 12 as keel 12'. Keel 12' includes several features which are identical to keel 12 of FIGS. 1-4, discussed above, and identical reference numerals have been used to indicate identical or substantially identical features therebetween. Keel 12' lacks stem engaging threads 36 positioned within second counterbore 32. Additionally, due to the absence of stem engaging threads 36, keel 12' is shorter than keel 12. The inclusion of keel 12' allows for the appropriate provisional keel, either keel 12 or keel 12', to be selected depending on the ultimate configuration of the final implanted components. Thus, when a final stem, similar to provisional stem 18, will be used with the final implanted components, keel 12 is selected. Alternatively, when a final stem will not be used with the final, implanted components, keel 12' may be selected.

Figure 7:
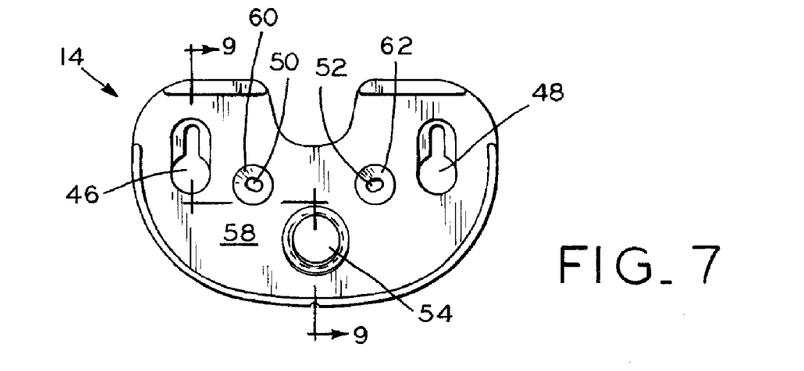
FIG. 7 is a plan view of the plate of the provisional prosthetic system of FIG. 1.
Figure 8:
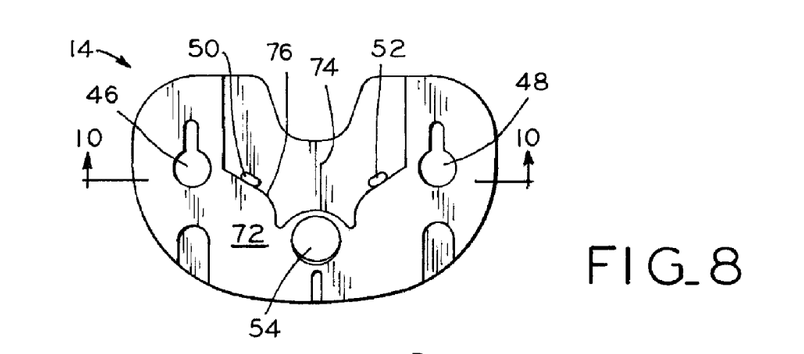
FIG. 8 is a bottom view of the plate of FIG. 7.
Figure 9:
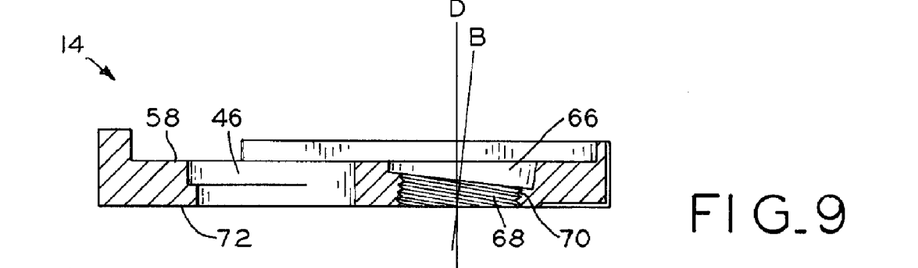
FIG. 9 is a cross-sectional view of the plate of FIG. 7 taken along line 9-9 of FIG. 7.
Figure 10:
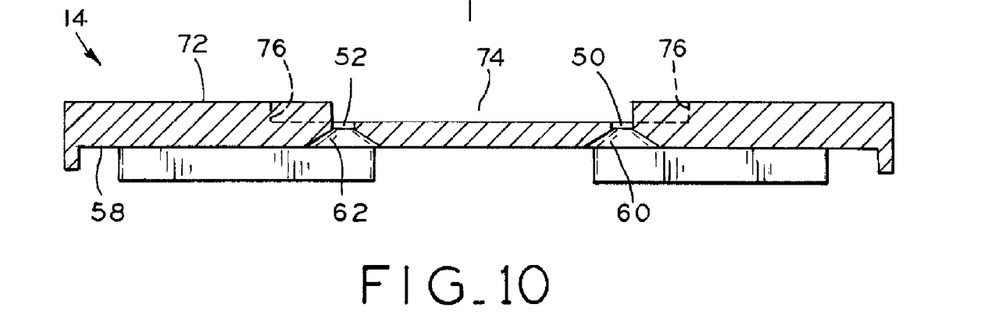
FIG. 10 is a cross-sectional view of the plate of FIG. 7 taken along line 10-10 of FIG. 8.

FIGS. 7-10 depict plate 14 configured for attachment to keel 12. In one embodiment, plate 14 is one of a plurality of plates 14 sized to replicate the orientation and/or size of at least one component of a modular prosthesis. As shown in FIG. 7, plate 14 includes fixation apertures 46, 48, alignment apertures 50, 52, and captured screw receiving aperture 54. Top surface 58 of plate 14 is partially recessed around alignment apertures 50, 52 to form countersinks 60, 62. Countersinks 60, 62 facilitate the passage of light to and through alignment apertures 50, 52. As discussed below, when plate 14 is properly aligned with keel 12, top surface 64 (FIG. 2) of fins 24 are visible through alignment apertures 50, 52. Thus, by facilitating the passage of light into alignment apertures 50, 52, countersinks 60, 62 increase the visibility of top surfaces 64 of fins 24. As shown in FIG. 9, captured screw receiving aperture 54 includes counterbore 66 and threaded bore 68. Captured screw receiving aperture 54 is angled along axis B, shown in FIG. 9, which helps prevent back out of captured screw 16, as described in detail below. Threaded bore 68 further includes threads 70 configured to engage external threads 42 of captured screw 16.

As shown in FIG. 8, plate 14 includes bottom surface 72, configured to be positioned atop keel 12. Recess 74 is formed within bottom surface 72 of plate 14 and defined by wall 76. Wall 76 is configured to abut at least a portion of fins 24 and body portion 22 of keel 12 when plate 14 is properly positioned relative to keel 12. Thus, the interaction of wall 76 with keel 12 provides a surgeon with tactile feedback indicating that plate 14 is properly positioned on keel 12. Additionally, with fins 24 of keel 12 properly abutting wall 76, at least a portion of top surfaces 64 of fins 24 are visible through alignment apertures 50, 52.

Figure 11:
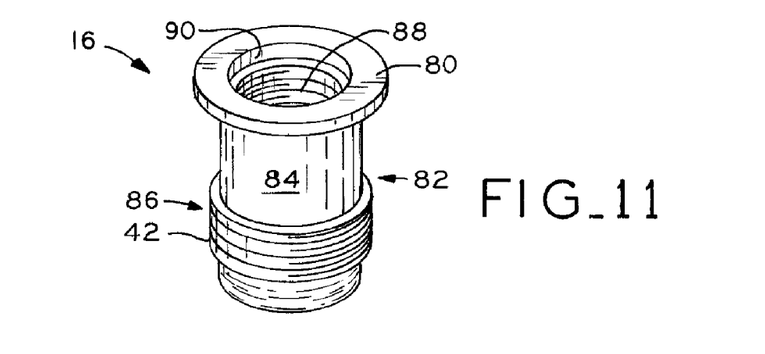
FIG. 11 is a perspective view of the captured screw of the provisional prosthetic system of FIG. 1.
Figure 12:
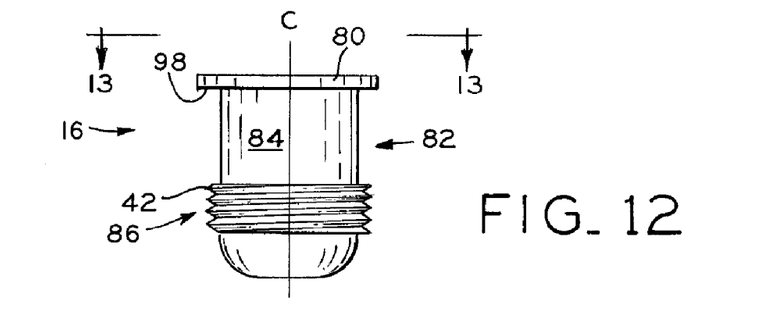
FIG. 12 is a front view of the captured screw of FIG. 11.
Figure 13:
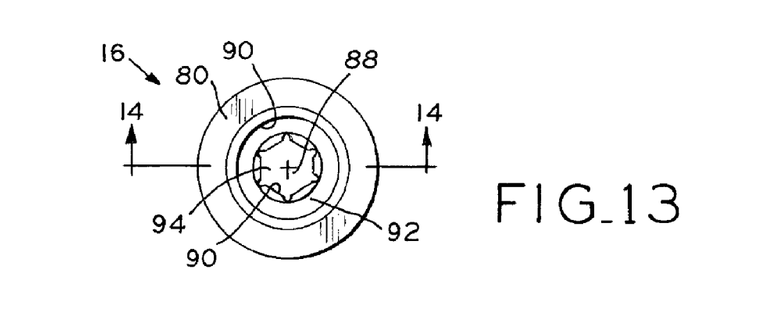
FIG. 13 is a plan view of the captured screw of FIG. 11.
Figure 14:
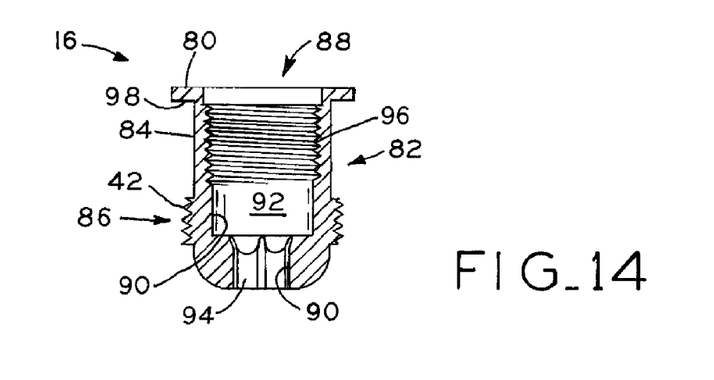
FIG. 14 is a cross-sectional view of the captured screw of FIG. 11, taken along line 14-14 of FIG. 13.
Figure 16:
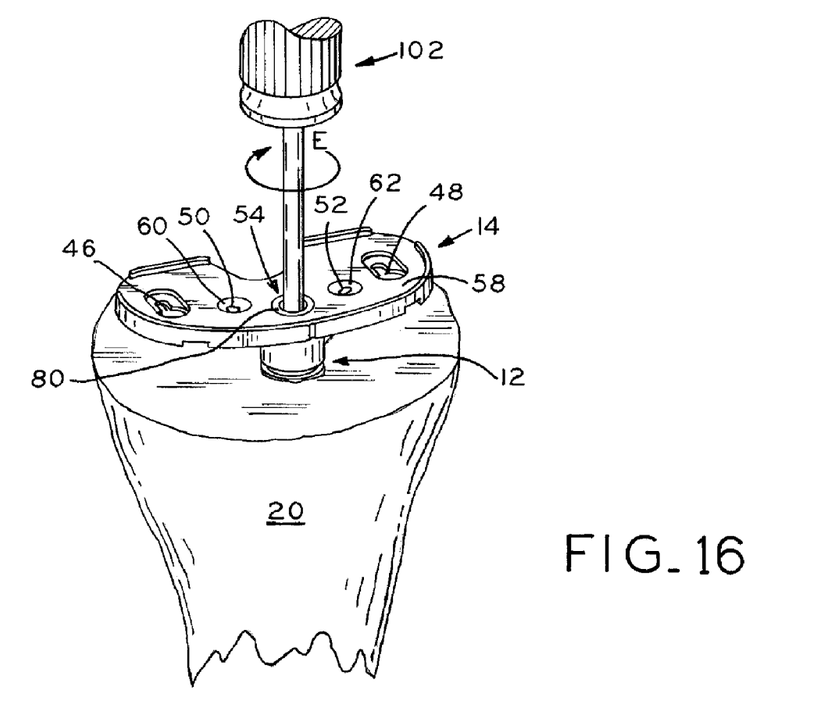
FIG. 16 is an assembly view of the provisional prosthetic system of FIG. 1, depicting the fastening of the plate to the keel.

Captured screw 16 is depicted in FIGS. 11-14. Referring to FIG. 11, captured screw 16 includes flange head 80 and external surface 82. External surface 82 includes non-threaded portion 84 and threaded portion 86. Threaded portion 86 of captured screw 16 is configured for threaded engagement with threaded bore 68 of plate 14 and captured screw engaging threaded portion 28 of keel 12. Captured screw 16 further includes internal bore 88 defined by internal wall 90. As shown in FIG. 14, internal wall 90 includes extraction portion 92 and securement portion 94. Extraction portion 92 of internal wall 90 includes threads 96 formed thereon. Threads 96 are configured for mating engagement with an extraction tool (not shown) to facilitate removal of captured screw 16, plate 14, and keel 12 after trialing. Internal wall 90 defines securement portion 94 as a hexagon configured for mating engagement with the hexagonal tip of drive tool, 102 (FIG. 16). While described and depicted herein as hexagonal, securement portion 94 may be any shape and/or may be threaded to facilitate engagement with a correspondingly configured drive tool.

With reference to FIGS. 1 and 15-17, the method of securing plate 14 to keel 12 via captured screw 16 is described. As stated above, captured screw 16 is designed to be retained within captured screw receiving aperture 54 (FIG. 7) of plate 14. As shown in FIG. 9, axis B of aperture 54 is offset relative to axis D, which is perpendicular to top and bottom surfaces 58, 72, respectively, of plate 14. Referring to FIG. 9, aperture 54 of plate 14 includes threads 70 which are aligned relative to axis B. By aligning longitudinal axis C of captured screw 16 (FIG. 12) with longitudinal axis B of captured screw receiving aperture 54 of plate 14, external threads 42 of threaded portion 86 will engage threads 70 (FIG. 9) of threaded bore 68 of captured screw receiving aperture 54. To advance captured screw 16 into receiving aperture 54 of plate 14, drive tool 102 (FIG. 16), configured for mating engagement with securement portion 94 of captured screw 16, is utilized. As drive tool 102 is rotated in the direction of the arrow E in FIG. 16, captured screw 16 is correspondingly rotated along longitudinal axes B, C and captured screw 16 is advanced through captured screw receiving aperture 54 of plate 14. Once threaded portion 84 of captured screw 16 is advanced entirely though threaded bore 68 of plate 14, non-threaded portion 84 of captured screw 16 is positioned within bore 68. Thus, captured screw 16 may be advanced unrestricted until bottom surface 98 of flanged head 80 contacts top surface 58 of plate 14.

In this position, removal of captured screw 16 is prevented by flanged head 80 and threaded portion 86. Additionally, accidental back out of captured screw 16 is substantially prevented due to the angular variation of longitudinal axis B of captured screw receiving aperture 54 and axis D of plate 14. Once in the "captured" position, movement of captured screw 16 is limited to unrestricted movement between a first position, in which flanged head 80 contacts the bottom of counterbore 66 of plate 14, and a second position, in which the uppermost thread of external threads 42 of captured screw 16 contacts bottom surface 72 of plate 14. Thus, the axial movement, i.e., movement of captured screw 16 along longitudinal axis D of FIG. 9, is correspondingly limited. Advantageously, the use of captured screw 16 allows for assembly of plate 14 and captured screw 16 prior to or during surgery. This may lessen surgical time and also ensure that captured screw 16 is available when needed to secure plate 14 to keel 12.

Figure 15:
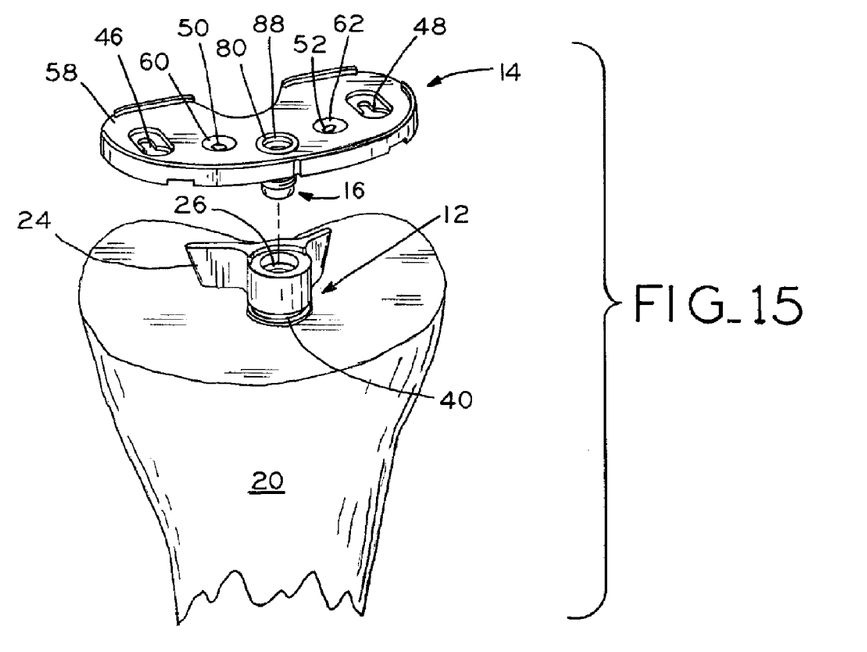
FIG. 15 is an assembly view of the provisional prosthetic system of FIG. 1, depicting the keel of the provisional prosthetic system implanted in the tibia.

With captured screw 16 retained through aperture 54 in plate 14, keel 12 may be inserted within bore 100 (FIG. 1) of tibia 20. Alternatively, keel 12 may be implanted prior to retention of captured screw 16 by plate 14. To position keel 12 within bore 100 an insertion tool (not shown) configured to mate with groove 40 of keel 12 may be used. Prior to insertion of keel 12, stem 18, if desired, may be attached to keel 12. Specifically, threaded shaft 44 of stem 18 may be inserted within second counterbore portion 32 of keel 12 to engage threads 36. Once securely attached to keel 12, stem 18 and keel 12 may be inserted within bore 100 of tibia 20 in the manner described above. Once positioned, as shown in FIG. 15, plate 14 and captured screw 16 may be secured to keel 12 by engaging external threads 42 on threaded portion 86 (FIG. 11) of captured screw 16 with threaded portion 28 of first counterbore portion 30 (FIG. 4) of keel 12.

As shown in FIGS. 16 and 17, drive tool 102 may be utilized to engage securement portion 94 (FIG. 14) of captured screw 16 and advance threaded portion 86 and captured screw 16 into bore 26 of keel 12. At any point during securement of plate 14 to keel 12, the alignment of plate 14 relative to keel 12 may be visually checked. Specifically, when plate 14 is properly aligned with keel 12, a portion of body 22 and fins 24 will abut wall 76 (FIG. 8) of keel 14. In this position, as described in detail above, at least a portion of top surface 64 of fins 24 will be visible through alignment apertures 50, 52 of plate 14. Thus, a portion of alignment apertures 50, 52 will be blocked by a portion of top surface 64 of fins 24. Advantageously, this provides an immediate visual indication to the surgeon that plate 14 and keel 12 are properly aligned.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A provisional prosthetic system, comprising:
a keel sized to replicate the orientation of at least one component of a modular prosthesis;
a plate sized to replicate the orientation of at least another component of a modular prosthesis, said plate having at least one substantially planar face and a threaded aperture extending therethrough, said aperture threaded about a longitudinal axis oblique to said at least one substantially planar face; and
a captured screw configured to secure said plate to said keel, said captured screw including a flanged head and an external surface, said external surface having a threaded portion and a non-threaded portion, said threaded portion of said captured screw configured to threadingly engage said thread aperture of said plate, wherein said threaded portion of said captured screw is advanced entirely through said aperture in said plate to retain said non-threaded portion of said captured screw within said threaded aperture of said plate.

2. The provisional prosthetic system of claim 1, wherein said keel further includes a threaded bore, said threaded bore configured to mate with said threaded portion of said captured screw to secure said plate to said keel.

3. The provisional prosthetic system of claim 1, wherein said keel further includes a fin extending therefrom, said plate having a recess configured to receive said fin therein to facilitate proper rotational alignment of said plate with said keel.

4. The provisional prosthetic system of claim 3, wherein said plate includes a second aperture, said fin visible through said second aperture when said fin is received within said recess of said plate.

5. The provisional prosthetic system of claim 1, wherein said captured screw further includes an internal wall defining a bore, said internal wall having a securement portion and an extraction portion, whereby said securement portion is configured to mate with a securing tool to secure said plate to said keel and said extraction portion is configured to mate with an extraction tool to facilitate extraction of said keel and said plate.

6. The provisional prosthetic system of claim 1, wherein said plate is a provisional tibial plate and said keel is a provisional tibial keel, 7. A method of assembling a provisional prosthetic component, comprising the steps of:
threading a threaded portion of a captured screw having a non-threaded portion through an aperture in a plate that is threaded about a first axis oblique to a substantially planar surface of the plate to position the non-threaded portion of the captured screw within the aperture;

orienting the plate relative to a fin extending from a keel, the plate sized to replicate the orientation of at least one component of a modular prosthesis and the keel sized to replicate the orientation of at least another component of a modular prosthesis;

visually confirming that the plate is properly oriented with respect to the fin of the keel through an aperture in the plate: and securing the plate to the keel by threading the threaded portion of the captured screw into a threaded bore in the keel.

8. The method of claim 7, wherein the orienting step further comprises receiving the fin within a recess in the plate.

9. The method of claim 7, further comprising, after the securing step, the step of implanting the provisional prosthetic component.

10. The method of claim 7. further comprising, before the orienting step. the step of implanting the keel.

11. The method of claim 7, wherein said plate is a tibial plate and said keel is a tibial keel.

* * * * *